(12) United States Patent
Weda et al.

(10) Patent No.: US 11,519,900 B2
(45) Date of Patent: Dec. 6, 2022

(54) ALIGNMENT OF BREATH SAMPLE DATA FOR DATABASE COMPARISONS

(71) Applicant: KONINKLIJKE PHILIPS N.V., Eindhoven (NL)

(72) Inventors: Johannes Weda, Nijmegen (NL); Teunis Johannes Vink, Valkenswaard (NL); Hugo Hubertus Knobel, Eindhoven (NL); Tamara Mathea Elisabeth Nijsen, Weert (NL)

(73) Assignee: Koninklijke Philips N.V., Eindhoven (NL)

( * ) Notice: Subject to any disclaimer, the term of this patent is extended or adjusted under 35 U.S.C. 154(b) by 677 days.

(21) Appl. No.: 16/479,775

(22) PCT Filed: Jan. 17, 2018

(86) PCT No.: PCT/EP2018/051039
§ 371 (c)(1),
(2) Date: Jul. 22, 2019

(87) PCT Pub. No.: WO2018/134214
PCT Pub. Date: Jul. 26, 2018

(65) Prior Publication Data
US 2021/0356453 A1    Nov. 18, 2021

Related U.S. Application Data

(60) Provisional application No. 62/449,146, filed on Jan. 23, 2017.

(51) Int. Cl.
*G01N 33/497* (2006.01)
*G01N 30/72* (2006.01)
(Continued)

(52) U.S. Cl.
CPC .......... *G01N 33/497* (2013.01); *A61B 5/082* (2013.01); *G01N 30/7206* (2013.01);
(Continued)

(58) Field of Classification Search
CPC ............. G01N 33/497; G01N 30/7206; G01N 30/8631; G01N 30/8686; G01N 2030/025;
(Continued)

(56) References Cited

U.S. PATENT DOCUMENTS

| | | | | |
|---|---|---|---|---|
| 2004/0096982 A1* | 5/2004 | Barnea | ................... | H01J 49/04 436/173 |
| 2006/0269945 A1* | 11/2006 | Kearney | ................ | G16B 20/00 435/6.12 |

FOREIGN PATENT DOCUMENTS

CN    105738434 A    7/2016

OTHER PUBLICATIONS

Smolinska, A. et al., "Profiling of Volatile Organic Compounds in Exhaled Breath As a Strategy to Find Early Predictive Signatures of Asthma in Children". PLOS One, vol. 9, Issue 4.

* cited by examiner

*Primary Examiner* — Benjamin R Schmitt
(74) *Attorney, Agent, or Firm* — Daniel H. Brean

(57) ABSTRACT

A method for synchronizing data for gas samples with volatile organic compounds. The data includes chromatographic data indicative of molecule retention times. The method includes identifying or selecting marker molecules and clustering the plurality of gas samples into a plurality of clusters according to a clustering criterion. Next, a first correction of retention time deviations is performed on the data for the gas samples between clusters by using the marker molecules as anchor points to provide a coarse reduction of retention time deviations between the data.
(Continued)

Finally, a second correction of retention time deviations is performed on the data, so as to further reduce retention time deviations between the data. The method reduces significant retention time deviations to allow, e.g., breath sample fingerprints obtained by different equipment at different times to be compared in one database for use on a digital platform.

15 Claims, 5 Drawing Sheets

(51) Int. Cl.
    *G01N 30/86*     (2006.01)
    *A61B 5/08*     (2006.01)
    *A61B 10/00*     (2006.01)
    *G01N 30/02*     (2006.01)

(52) U.S. Cl.
    CPC ..... G01N 30/8631 (2013.01); G01N 30/8686 (2013.01); *A61B 2010/0087* (2013.01); *G01N 2030/025* (2013.01); *G01N 2033/4975* (2013.01)

(58) Field of Classification Search
    CPC ............ G01N 2033/4975; A61B 5/082; A61B 2010/0087
    See application file for complete search history.

ALIGNMENT OF BREATH SAMPLE DATA FOR DATABASE COMPARISONS

CROSS-REFERENCE TO RELATED APPLICATIONS

This patent application claims the priority benefit under 35 U.S.C. § 371 of international patent application no. PCT/EP2018/051039, filed Jan. 17, 2018, claims the priority benefit under 35 U.S.C. § 119(e) of U.S. Provisional Application No. 62/449,146 filed on Jan. 23, 2017, the contents of which are herein incorporated by reference.

FIELD OF THE INVENTION

The invention relates generally to analysis of gas. Especially, the invention relates to a method and a device suited for medical analysis of gas, e.g. breath exhaled from a person or gas based on samples from skin, urine or feces. More specifically, the invention relates to a method and a system for retention time synchronizing or aligning breath fingerprints based on spectrography data, e.g. from GC-MS or micro-GC systems, to allow database comparisons across time and across different equipment.

BACKGROUND OF THE INVENTION

Exhaled breath analysis in health and disease is an area of growing clinical interest. Using breath as a biological sample is appealing, because breath-collection is cheap, easy to perform and non-invasive. Volatile Organic Compounds (VOCs) are excreted from the skin, urine, feces and most notably via exhaled breath. Besides of pulmonary origin, VOCs may also originate from the blood, reflecting physiological, pathological or pathogen related biochemical processes throughout the body. As such exhaled breath analysis may allow metabolic fingerprinting of disease processes anywhere inside the body.

Several studies have shown the diagnostic potential of these techniques in clearly defined subsets of patients with various diseases. The volatiles in exhaled breath change when an illness is present, and specific markers can be linked to specific diseases. The detection of these specific markers in very low amount in a complex matrix of other volatile compounds present in exhaled breath, is a challenge for even the state of the art analysis techniques.

The gold standard analysis of VOCs is based on chemical analytical techniques such as Gas Chromatography Mass-Spectrometry (GC-MS). This technique provides knowledge on individual molecular compounds and thereby extends our understanding on disease pathophysiology. A miniaturized GC system, or other separation method, can also be used to separate the volatiles. Several studies have shown the diagnostic potential of these techniques in clearly defined subsets of patients with various diseases.

However, the implementation of these techniques into clinical settings is currently hampered by inter- and intra-device differences. While separation techniques such as provided by the column in GC systems are important to specifically measure compounds of interest and thus create breath fingerprints, the wearing and aging of the column causes retention time shifts that complicate comparisons over time. To synchronize the GC-MS data different solutions are being used. One solution is the use of pre-processing software, where the retention time alignment in e.g. the XCMS package works very well for relatively small retention time shifts. This software package is currently the most cited pre-processing tool in the metabolomics literature. Another solution is to use molecules from the measured chromatogram as anchor points to align all chromatograms to each other. The used molecules can either be already present in the originally measured sample, or added later to allow for normalization, identification and alignment purposes.

For the use of breath analysis across the health care continuum it is important to be able to accurately compare samples measured at different moments in time, and on different platforms or machines. In fact, for integration of breath analysis results in database systems, e.g. cloud based storage and analysis, such as the health suite digital platform (HSDP), a standardization of the measurements will provide a large advantage. Such systems only allow analysis of this Big Data when the data is added in a unified manner.

SUMMARY OF THE INVENTION

Following the above, the inventors of the present invention have appreciated that it is a problem to be able to accurately compare breath fingerprints over time and to allow integration of such data into digital platforms, and especially accurate correction of retention time deviations is an important parameter for such integration.

In particular, it may be seen as an object of the present invention to provide a device and method that solves the above mentioned problems, or other problems, of the prior art.

In a first aspect, the invention provides a computer implemented method for synchronizing data for a plurality of gas samples with volatile organic compounds, such as gas samples obtained as breath exhaled from a subject, the method comprising receiving, for each of the plurality of gas samples, chromatographic data indicative of molecule elution times, identifying at least one marker molecule, preferably exhibiting distinct peaks, in the chromatographic data for each of the plurality of gas samples, clustering the plurality of gas samples into a plurality of clusters according to a clustering criterion, performing a first correction of retention time deviations on the data for the plurality of gas samples between clusters by using the marker molecule as anchor points, so as to reduce retention time deviations between the data for the plurality of gas samples, such as using a polynomial fitting function on retention time of the marker molecule, and performing, after said first correction, a second correction of retention time deviations on the data for the plurality of gas samples, so as to further reduce retention time deviations between the data for the plurality of gas samples.

Such method is advantageous, since the inventors have realized that it is possible to time synchronize or time align even data obtained from gas samples over long periods in time, thereby allowing integration of e.g. breath fingerprint data on digital platforms. Hereby, breath samples obtained and analyzed at different apparatus at different periods of time can be integrated on the digital platforms to form valuable clinical information databases.

Specifically, the method is suitable for synchronizing or time aligning data based on analysis of the gas samples by a Gas Chromatography-Mass Spectrography (GC-MS) or a Liquid Chromatrography-Mass Spectrography (LC-MS) analysis process if the gas samples are transformed into a liquid. Additional mass spectrography data for the gas samples can advantageously be applied also in the method to improve identification of molecules. Especially, the method may be arranged to operate on data provided by such GC-MS or LC-MS devices, or a pre-processed version of data from such devices. The devices and methods for obtaining GC-MS or LC-MS data as well as details regarding these data themselves are out of the scope of the present invention, but known by the skilled person.

The method is advantageous, since it works without the need to add molecules to the gas samples to allow alignment afterwards, which possibly disturbs and/or confuscates the original gas sample.

In the first time correction, it is possible to correct larger retention time deviations exceeding what is possible with existing processing toolboxes. The second time correction step to further reduce retention time deviations may be performed by applying existing processing toolboxes.

The method can be implemented as stand alone software or integrated in existing digital platform software packages.

In the following, preferred embodiments or features of the first aspect will be described.

The step of identifying one or a plurality of marker molecules may comprise detecting intensity peaks in the chromatographic data indicative of molecule elution times. The marker molecule(s) are preferably so-called easily identifiable molecules (EIMs). E.g. the identification of marker molecule(s) may be supported by mass spectrography and comparison with database or lookup table data, in case such mass spectrography data are also available for the plurality of gas samples. The step of identifying at least one marker molecule preferably comprises identifying a plurality of marker molecules. Especially, such as 5-20 marker molecules, e.g 8-12 marker molecules, may be selected for the following steps. Further, it is preferred that the step of identifying marker molecule(s) comprises selecting at least two marker molecules which have retention times differing more than 200 seconds, e.g. more than 300 seconds, however this is understood to depend on the actual chromatography data and equipment used to provide the data. Most preferably, a plurality of marker molecules are selected, such that the marker molecules represent molecules having retention times covering at least the majority of retention time range of interest, so as to obtain the best time synchronization over the retention time range of interest. E.g. it may be preferred that marker molecules are selected to be evenly spread covering the retention time of interest. The plurality of marker molecules preferably comprises at least one molecule, such as at least two molecules, selected from: Acetone, Isoprene, Ethylacetate, Benzene, Pentanal, Methylcyclohexane, Toluene, Octane, Styrene, α-pinene, Propylbenzene, Phenol, α-methylstyrene, and d-limonene. The plurality of marker molecules may especially comprise at least one of: Benzene and Toluene, such as both of Benzene and Toluene. These molecules are preferred as marker molecules, since they are frequently present in exhaled breath, and they are easy to identify due to abundant presence or distinctive mass spetograms. It is to be understood that other molecules may be selected as marker molecules in case other types of gas samples are to be analyzed. The step of identifying the marker molecule(s) may comprise identifying at least one marker molecule which is present only in a subset of the plurality of gas samples, however it may also be preferred to select molecules present in all of the plurality of gas samples.

The step of clustering is preferably performed according to a clustering criterion involving retention times for the marker molecule(s) in the plurality of gas samples, such as a clustering criterion serving to minimize marker molecule (s) retention time deviation within clusters. The step of clustering is preferably performed according to a clustering criterion involving information about the plurality of gas samples, such as information about a time and date for obtaining each of the plurality of gas samples have been obtained, thereby allowing clusters with gas samples obtained with the same device or at the same period of time to be clustered together.

The step of performing the first correction may comprise calculating a polynomial fitting function, such as a linear or higher order polynomial fitting function, on retention times of the marker molecule(s). The step of performing the first correction preferably comprises iteratively identifying marker molecule(s) and subsequently performing retention time corrections, until a predetermined stop criterion is met.

The method preferably comprises receiving, for each of the plurality of gas samples, mass spectrometric data, wherein the method comprising analyzing said mass spectrometric data to identify molecules in the gas samples. Preferably, the method comprises receiving GC-MS data for each of the plurality of gas samples. Especially, the method may comprise comparing the mass spectrometric data with database mass spectra to indentify molecules in the gas samples.

The second correction of retention time deviations is preferably performed by applying one or more of known processing toolboxes, e.g. the time alignment algorithm known from the toolbox XCMS, which is known in the field, and further described in Smith, C. A., et al., XCMS: Processing mass spectrometry data for metabolite profiling using Nonlinear peak alignment, matching, and identification. Analytical Chemistry, 2006. 78(3): p. 779-787.

In a second aspect, the invention provides a computer program product comprising computer executable program code which, when executed on a processor, causes the processor to perform the method according to the first aspect. Especially, the program code may be present on a tangible storage medium and/or available in a downloadable form.

In a third aspect, the invention provides a breath analysis system comprising a device arranged to receive, for each of a plurality of gas samples obtained as breath exhaled from a subject, chromatographic data indicative of molecule elution times, and a processor programmed to perform the method according to the first aspect, and to subsequently analyze the chromatographic data for the plurality of gas samples in accordance with an analysis algorithm, and to a provide an output accordingly.

Especially, the system may comprise a computer or server.

Especially, the breath analysis system may comprise a gas inlet comprising a mouthpiece arranged on an exterior part of its casing, so as to allow the subject, a person or an animal, to directly breathe into the mouthpiece and thus provide a gas sample to be analysed. Other tube fittings may be used for connection to receive breathed air from a mechanical ventilator, e.g. in intensive care units, to which the subject is connected. Still further, the gas inlet of the device may be arranged for mounting of a gas bag with the gas sample to be analyzed.

The system may further comprise a chromatographic analyzer arranged to receive the plurality of gas samples obtained as breath exhaled from the subject, and to provide chromatographic data indicative of molecule elution times, for each of the plurality of gas samples accordingly. Especially, the system may comprise a GC-MS analyzer arranged to provide respective mass spectrography data, in addition to the chromatography data, in response to the plurality of gas samples.

In general, it is appreciated that the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIG. 7a shows before time alignment, FIG. 7b shows after the first time correction, and FIG. 7c shows the final result after the second time correction.

DESCRIPTION OF EMBODIMENTS

Figure 1:
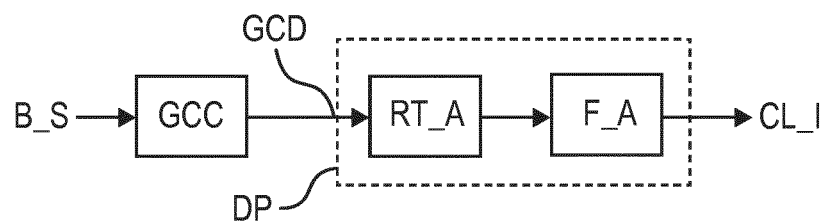
FIG. 1 illustrates a block diagram of a breath analysis system embodiment.

FIG. 1 illustrates a block diagram of a breath analysis system embodiment with a digital platform DP comprising a computer or server, e.g. the cloud based health suite digital platform HSDP, incorporating breath sample B_S analysis data for clinical information CL_I e.g. to assist in diagnosing diseases based on volatile organic compounds in the gas sample B_S. The DP involves processing software implementing the synchronization method RT_A for retention time alignment according to the first aspect of the invention. The DP system may combine and compare breath fingerprints collected over time and measured on different machines. The approach may cover other metabolomics methods using MS or selective detection such as LC-MS data.

Based on a gas sample B_S obtained as a sample of breath collected from a subject, the gas sample B_S is analyzed in an analyzer preferably comprising a GC column device GCC. The GC column device GCC may be a GC-MS analyzer, as known in the art, and the output data GCD preferably comprises mass spectrography data in addition to the chromatography data. Alternatively, the analyzer may be a LC-MS analyzer, as also known in the art.

The output from the analyzer GCC is chromatographic data GCD which is applied to the DP which is arranged to receive, for each of a plurality of gas samples B_S, chromatographic data GCD indicative of molecule elution times, and a processor in the DP is programmed to perform the retention time synchronization or alignment method RT_A according to the invention, and to subsequently analyze the chromatographic data for the plurality of gas samples B_S in accordance with a further analysis algorithm F_A, and to a provide a clinical information output CL_I accordingly. Such further analysis F_A is known in the art and will not be described further, since it is not the scope of the present invention. However, the retention time correction algorithm RT_A according to the invention allows a higher quality of data for such further analysis algorithms F_A and thereby allows clinical information CL_I with higher quality for detection of diseases and e.g. other information of medical interest.

Figure 2:
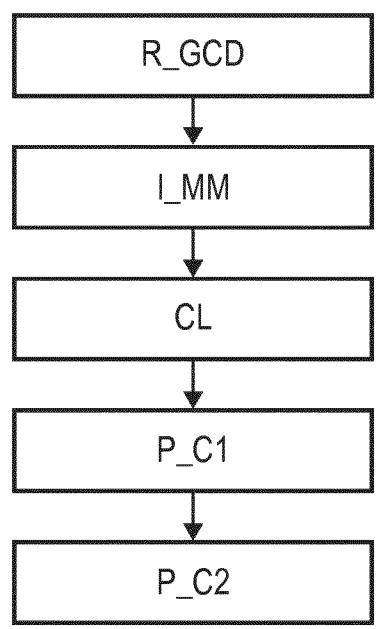
FIG. 2 illustrates steps of a retention time alignment method embodiment.

FIG. 2 illustrates steps of a retention time synchronization method embodiment, i.e. an embodiment of the method to be implemented as the retention time alignment algorithm RT_A in software in the DP in the system shown in FIG. 1. The method comprises receiving R_GCD, for each of the plurality of gas samples, chromatographic data indicative of molecule elution times, preferably the input data for each gas sample also comprises mass spectrography data. As mentioned, e.g. the data may be in the form known as output from existing GC-MS analyzing equipment.

Figure 3:
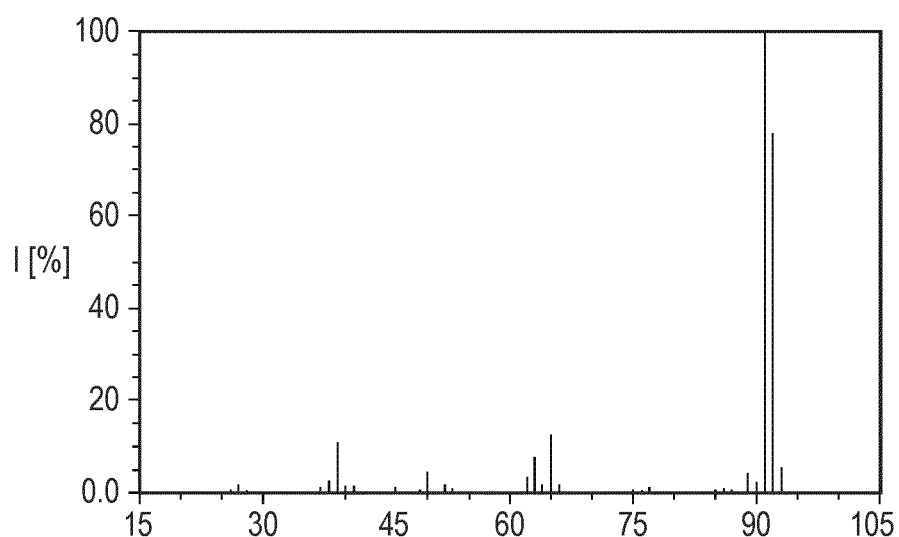
FIG. 3 illustrates an example of a mass spectrum for Toluene.

As a first step in the processing algorithm, the method comprises identifying I_MM a plurality of marker molecules in the chromatographic data for each of the plurality of gas samples. Preferably, the marker molecules are identified as the co-called easy identifiable molecules (EIMs). This step is applied after peaks are detected in the GC-MS data, using for example the matched filtration and peak identification, e.g. algorithms which can be found in the known XCMS software package. Then, molecules commonly present in most samples and which have a clearly identifiable mass spectrum are selected as marker molecules. These selected marker molecules then serve as marker molecules or anchor points. Preferably, marker molecules are selected which exhibit distinct mass spectra with distinct peaks in their mass spectra. Molecules containing carbon rings (aromatics) generally have such spectra, while linear hydrocarbons do not. Examples are benzene (low abundance) and toluene (rather abundantly present and clearly identifiable due to the benzene ring by fragments m/z=91, 92). Additionally, each part of the retention time window needs to be represented by EIMs, such that time shifts in every part of the full time window can be corrected for. For a good result 5-20, such as about 10, of such EIMs need to be selected based on the data in the available gas samples, and further based on input from an operator according to the operator's experience. The marker molecules are preferably identified as follows. Each EIM is expected to elute in a certain time window, characteristic for that molecule. Toluene, for example, typically elutes around 10 minutes. For each marker molecule the expected mass spectrum is known according to the known databases. Alternatively user libraries containing mass spectra from known compounds or standards can also be used, or other large databases. FIG. 3 shows, as an example, the mass spectrum for toluene. Within the time window associated with the marker molecule all mass spectra are compared to the known mass spectrum of the marker molecule. To calculate the similarity between mass spectra, the spectra are represented as vectors. The cosine of the angle between the factors may be calculated using the dot-product function, and is used as a similarity measure. Such algorithm provides a suitable similarity estimate between mass spectra.

Preferred candidates for EIM to be used in the alignment procedure, especially in case of gas samples being breath exhaled by a human, are given in the below table. It may be preferred to use at least Benzene and Toluene, but it may be preferred to include also one or more from the table with higher retention times.

| Molecule | Formula | Molecular mass | Signature mass fragment |
|---|---|---|---|
| Acetone | C3H6O | 58 | 58 |
| Isoprene | C5H5 | 68 | 67 |
| Ethylacetate | C4H8O2 | 88 | 88 |
| Benzene | C6H6 | 78 | 78 |
| Pentanal | C5H10O | 86 | 58 |
| Methylcyclohexane | C7H14 | 98 | 70 |
| Toluene | C7H8 | 92 | 92 |
| Octane | C8H18 | 114 | 114 |
| Styrene | C8H8 | 104 | 104 |
| α-pinene | C10H16 | 136 | 136 |
| Propylbenzene | C9H12 | 120 | 120 |
| Phenol | C6H6O | 94 | 94 |
| α-methylstyrene | C9H10 | 118 | 118 |
| d-limonene | C10H16 | 136 | 121 |

Next, the method comprises clustering CL the plurality of gas samples into a plurality of clusters according to a clustering criterion. Preferably, the clustering is performed in accordance with the retention time of the EIMs. Additionally or alternatively, other information on the samples can also be used for clustering, such as whether the samples are measured closely in time on the same analyzer machine. E.g. the gas samples may be measured in batches, resulting is little retention time deviations between the samples within each batch, and larger deviations between the samples in different batches.

Figure 4:
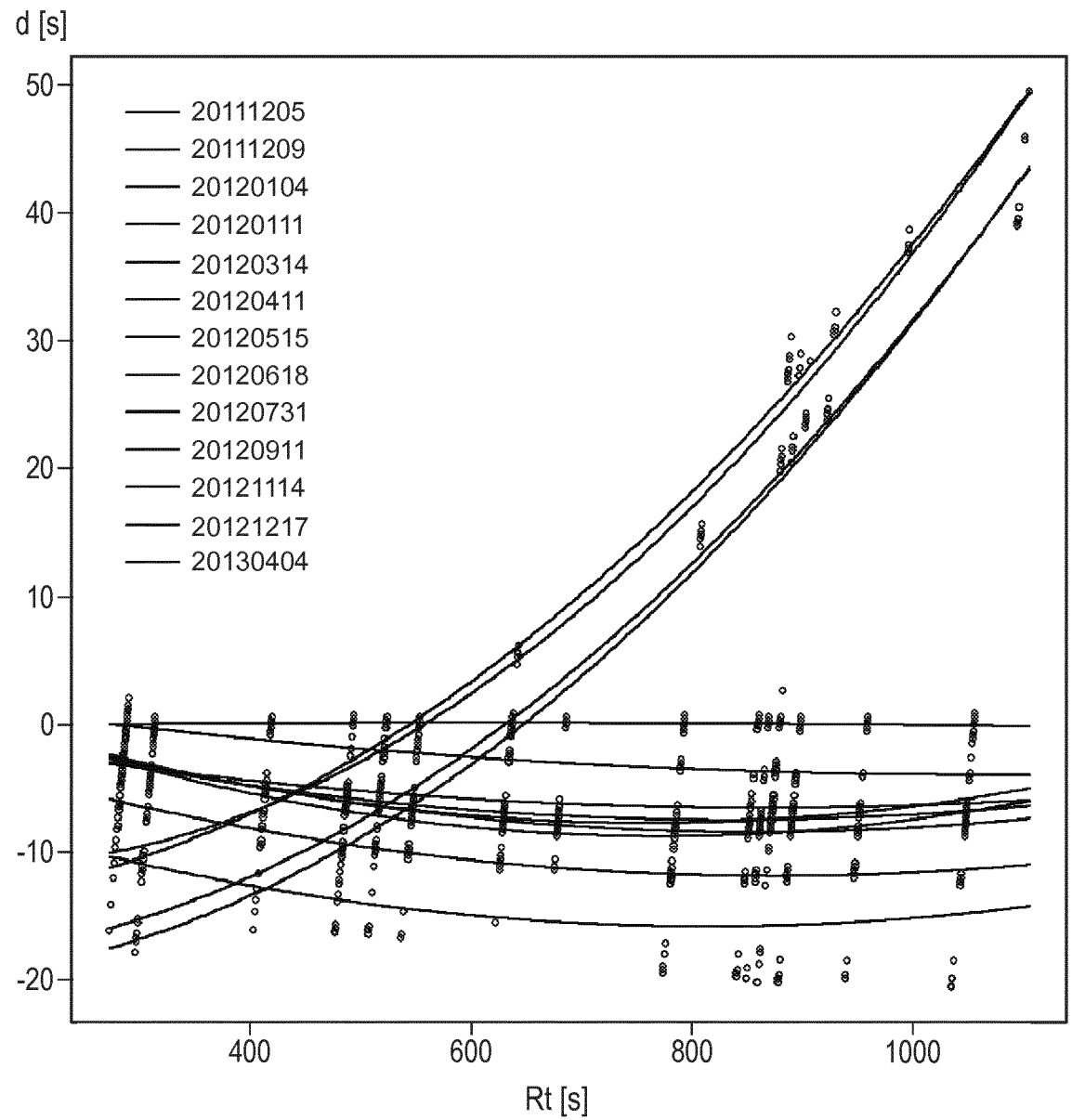
FIG. 4 illustrates a graph with example retention time shifts as a function of retention time for selected molecules detected in gas samples from different batches obtained at different periods.

FIG. 4 shows a graph with example data indicating an initial spread in retention time shift d as a function of retention time Rt for molecules from the above table. The solid lines indicate quadratic fits through the data points. The example is based on gas samples obtained in different batches, at different periods in time. One batch (the one labelled 20120314) is taken as a reference since it contains many samples and is measured about halfway in the total time covered by the batches. The retention time shifts d are seen to be rather large, ranging from 20 seconds at low retention times Rt to 60 seconds at large retention times Rt. Note also the large difference in retention time shift d between the four highest curves and all other curves. The upper curves are measured until a specific date, where the analyzing GC column was replaced by a new one, causing a completely different retention time Rt pattern in the rest of the measurements.

The next step is performing P_C1 a first correction of retention time deviations on the data for the plurality of gas samples between clusters by using the marker molecules as anchor points, so as to reduce retention time deviations d between the data for the plurality of gas samples. This may be performed by fitting marker molecules (EIMs) using a linear or higher order polynomial function. Based on the fit, the first raw retention time collection is performed on the full retention time range. The identification of the marker molecules and the subsequent retention time correction can be iteratively performed until no improvement, or only improvement below a set threshold, is obtained.

Figure 5:
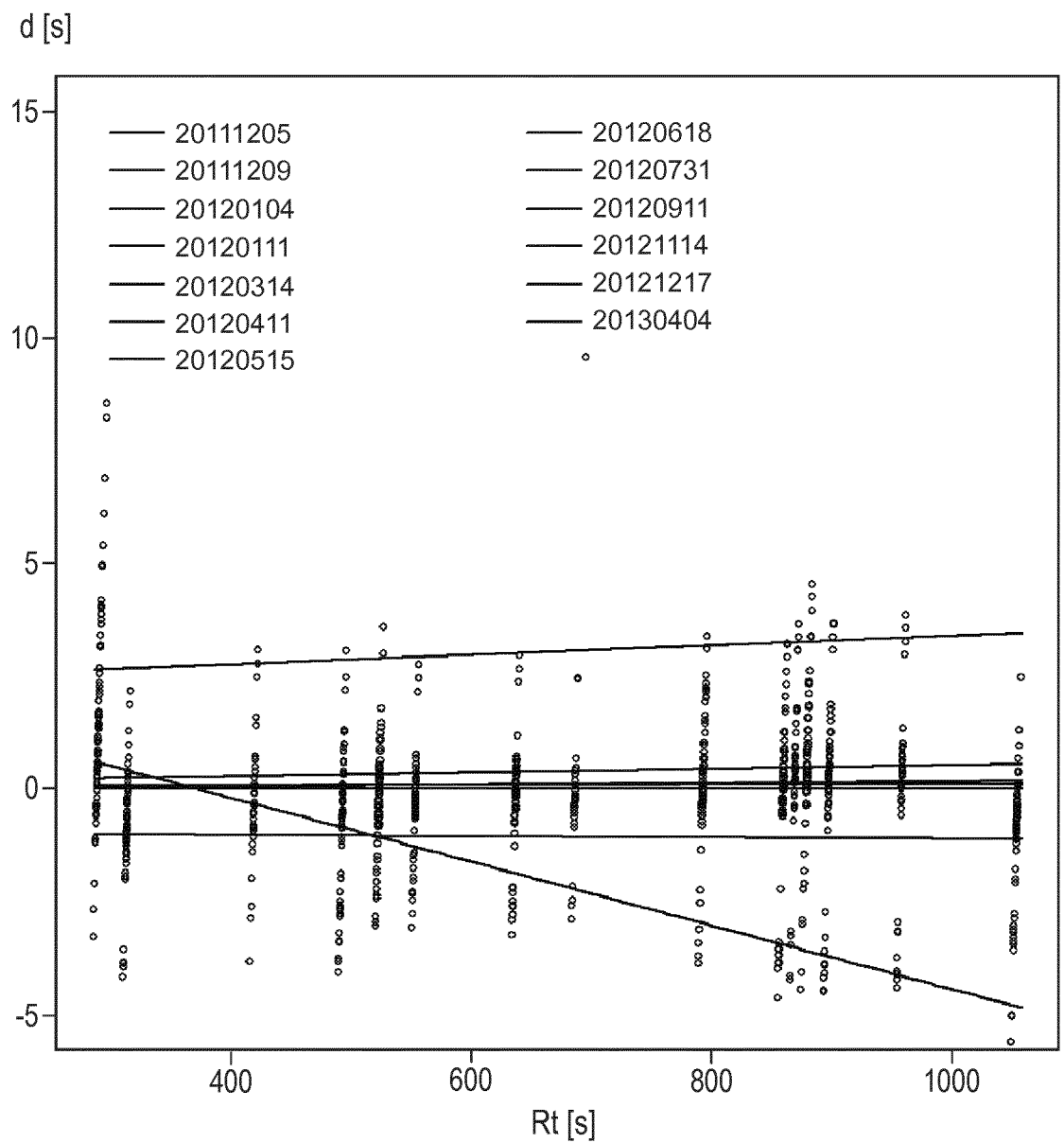
FIG. 5 illustrates a graph with retention time shifts as a function of retention time for the same molecules and batches as in FIG. 4, but corrected according to the first time correction of the invention.

FIG. 5 illustrates for the same example data from FIG. 5 the result of the first retention time correction. The retention time shifts d are now much lower, only about 10 seconds for the full retention time range Rt. The solid lines indicate linear fits through the data points.

As the last step, after the first coarse correction of retention time deviations P_C1, the method comprises performing a second time correction P_C2 of retention time deviations on the data for the plurality of gas samples, so as to further reduce retention time deviations d between the data for the plurality of gas samples. A linear fit, or other fit function, can be made through the data points per batch, and used as the basis for performing the second retention time correction P_C2. The second retention time correction P_C2 may be performed by the time alignment algorithm known from the XCMS toolbox or other standard software package or similar algorithm. Specifically, it may be preferred that the second retention time correction P_C2 comprises first matching peaks across samples and grouping them together, then 'well behaved' groups are identified. These peak groups contain very few samples which have no peaks assigned and very few samples which have more than one peak assigned. Because of these conditions, well behaved groups have a high probability of containing properly matched peaks. The alignment is performed by calculating the median retention time in each of those peak groups, and correcting all retention times accordingly. Since the well behaved peak groups are typically evenly distributed over a significant part of the retention time range, a detailed correction can be calculated for this range. The method is preferably iteratively applied. At each iteration cycle the peak grouping parameters are narrowing down until a satisfactory alignment is obtained.

Figure 6:
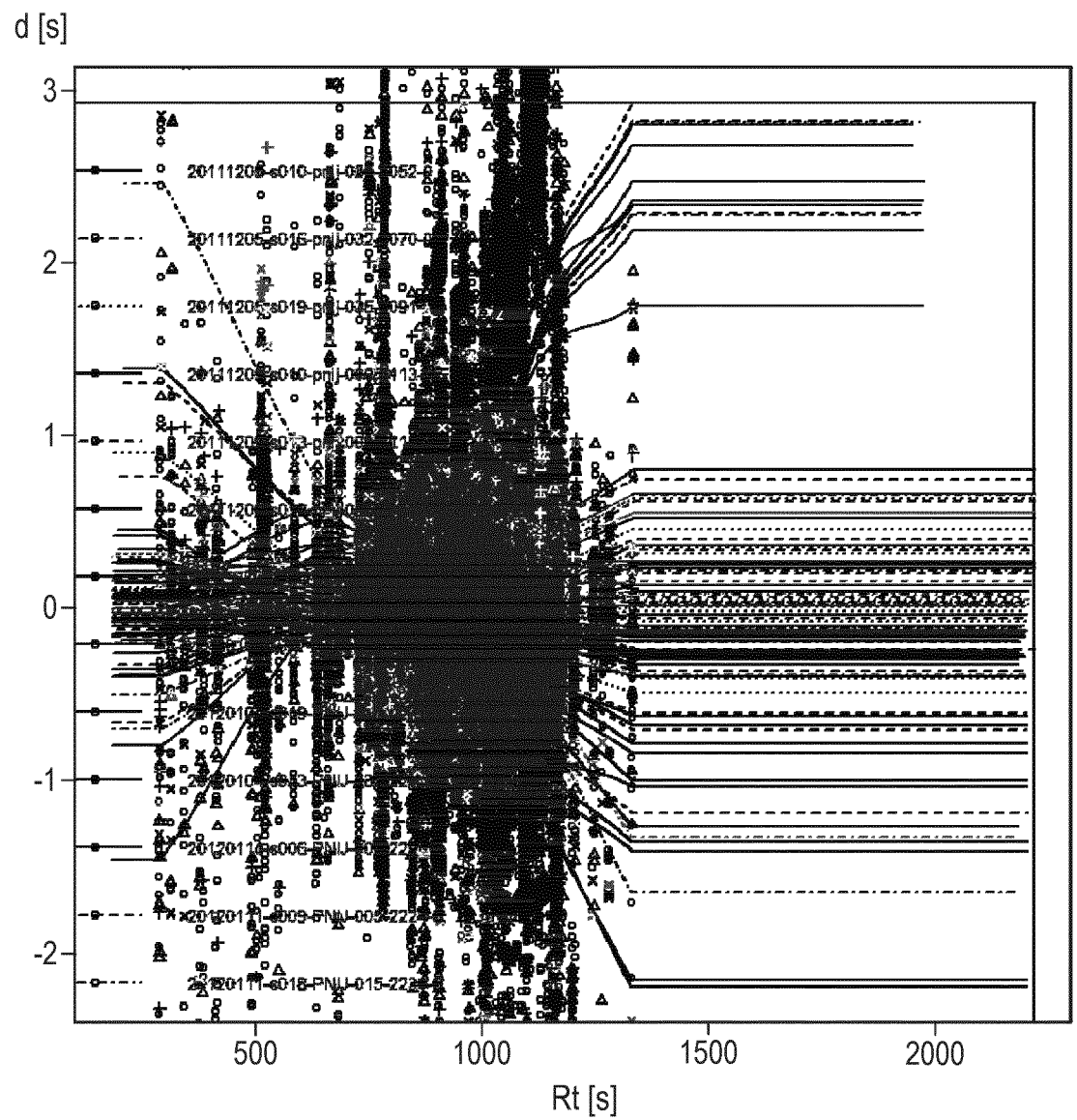
FIG. 6 illustrates a graph with retention time shifts as a function of retention time for the same molecules and batches as in FIG. 5, but now corrected also according to the second time correction of the invention.

FIG. 6 shows a graph of the example data after the second retention time correction P_C2 has been applied. As seen, the retention time deviations d are now further reduced.

Figure 7A:
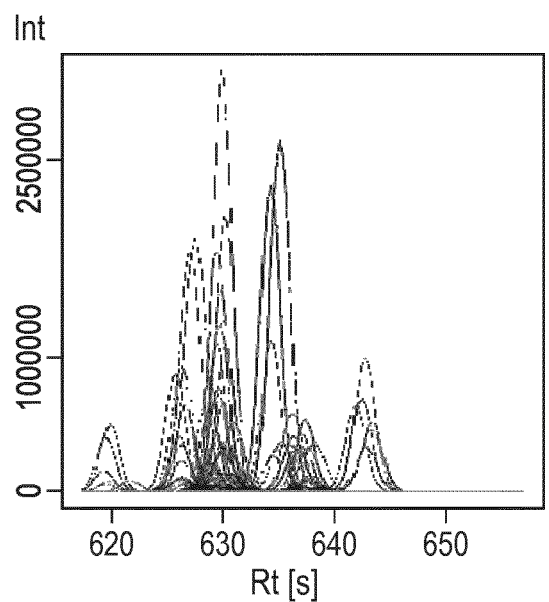
FIGS. 7a-7c illustrate graphs showing signature fragment of Toluene as a function of retention time for different batches of gas samples.
Figure 7B:
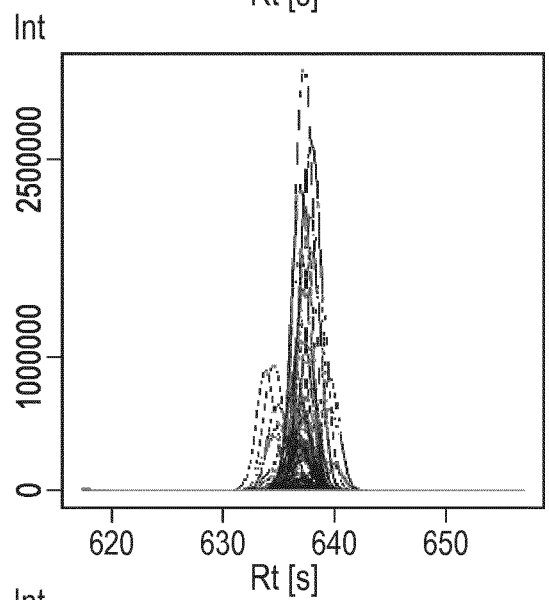
Figure 7C:
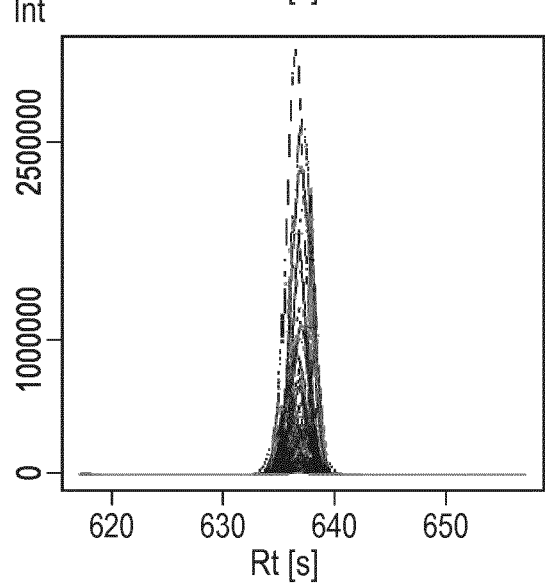

FIGS. 7a-7c illustrate the final quality of the alignment can be inspected by looking at the behaviour of the signature mass fragments of the marker molecules. The intensity of signature fragment 92 of toluene is plotted against the retention time for three steps in the alignment procedure: FIG. 7a: raw, no alignment performed yet, FIG. 6b: after the first retention time correction, and FIG. 7c: after the second retention time correction. Different curves represent different gas samples. It can be seen that the peaks of the fragment align during the alignment procedure. In FIG. 7c the peaks are all aligned, showing that the procedure has successfully worked.

All the steps above preferably result in an ion-fragment peak table. Each row in such table corresponds with a sample. The first few columns contain sample and patient data, such as sample data, age, gender and illnesses. The remaining columns may contain the abundances of the peaks, or ion-fragments. Typically, there are a few thousand of those. This table serves as input for further statistical analysis.

It is understood that the method may comprise or be used in connection with a further analysis of the data, e.g. diagnosing a disease based on a result of analysing exhaled breath from a subject according to the gas sample synchronizing method. The method may further comprise initiating a specific therapy, e.g. a medical treatment of Tuberculosis. Further, breath VOC analysis may be used for monitoring/analysis of lung cancer, breast cancer, other types of cancer, or respiratory infections. Also, breath analysis may be applicable for monitoring diseases such as asthma and Chronic Obstructive Pulmonary Disease (COPD) e.g. response to treatment, exacerbation monitoring. Furthermore, breath analysis may further be applied for monitoring glucose level in diabetes. Still further, an application example may be monitoring for sepsis and necrotizing enterocolitis (NEC) from VOC analysis based on gas analysis based on feces in neonates.

To sum up, the invention provides a method RT_A for synchronizing data for a plurality of gas samples, e.g. breath samples, with volatile organic compounds. The data comprises chromatographic data indicative of molecule elution times, and preferably also mass spectrography data. The method comprises identifying or selecting I_MM marker molecules, e.g. 5-20 molecules, preferably easily identifiable molecules for each of the plurality of gas samples, and clustering CL the plurality of gas samples into a plurality of clusters according to a clustering criterion, e.g. including additional information such as time of obtaining the data and/or analyzing equipment used. Next, a first correction of retention time deviations P_C1 is performed on the data for the gas samples between clusters by using the marker molecules as anchor points, so as to provide a coarse reduction of retention time deviations d between the data for the gas samples. Finally, a second correction of retention time deviations P_C2 on the data for the gas samples, so as to further reduce retention time deviations d between the data for the gas samples, e.g. by using standard software packages. The method can reduce significant retention time deviations so as to allow e.g. breath sample fingerprints obtained by different equipment at different periods of time to be compared in one database for use on a digital platform DP such as the HSDP.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer implemented method for synchronizing data for a plurality of gas samples with volatile organic compounds, the method comprising
   receiving, for each of the plurality of gas samples, chromatographic data indicative of molecule retention times,
   identifying at least one marker molecule in the chromatographic data for each of the plurality of gas samples,
   clustering the plurality of gas samples into a plurality of clusters according to a clustering criterion,
   performing a first correction of retention time deviations on the data for the plurality of gas samples between clusters by using the at least one marker molecule as anchor points, so as to reduce retention time deviations between the data for the plurality of gas samples, and
   performing, after said first correction, a second correction of retention time deviations on the data for the plurality of gas samples, so as to further reduce retention time deviations between the data for the plurality of gas samples.

2. The method according to claim 1, wherein the step of identifying at least one marker molecule comprises detecting intensity peaks in the chromatographic data indicative of molecule retention times.

3. The method according to claim 1, wherein the step of identifying at least one marker molecule comprises identifying 5-20 marker molecules.

4. The method according to claim 1, wherein the step of identifying at least one marker molecule comprises selecting at least two marker molecules which have retention times differing more than 200 seconds.

5. The method according to claim 1, wherein the at least one marker molecules comprises at least one molecule selected from: Acetone, Isoprene, Ethylacetate, Benzene, Pentanal, Methylcyclohexane, Toluene, Octane, Styrene, α-pinene, Propylbenzene, Phenol, α-methylstyrene, and d-limonene.

6. The method according to claim 5, wherein the at least one marker molecule comprises at least Benzene and Toluene selected as marker molecules.

7. The method according to claim 1, wherein the step of identifying at least one marker molecule comprises identifying at least one marker molecule which is present only in a subset of the plurality of gas samples.

8. The method according to claim 1, wherein the step of clustering is performed according to a clustering criterion involving retention times for the at least one marker molecule in the plurality of gas samples.

9. The method according to claim 1, wherein the step of clustering is performed according to a clustering criterion involving information about the plurality of gas samples.

10. The method according to claim 1, wherein the step of performing the first correction comprises calculating a polynomial fitting function, on retention times of the at least one marker molecule.

11. The method according to claim 1, wherein the step of performing the first correction comprises iteratively identifying the at least one marker molecule and subsequently performing retention time corrections, until a predetermined stop criterion is met.

12. The method according to claim 1, receiving, for each of the plurality of gas samples, mass spectrometric data, the method comprising analyzing said mass spectrometric data to identify molecules in the gas samples.

13. A computer program product comprising computer executable program code which, when executed on a processor, causes the processor to synchronize data for a plurality of gas samples with volatile organic compounds, comprising
   receiving, for each of the plurality of gas samples, chromatographic data indicative of molecule retention times,
   identifying at least one marker molecule in the chromatographic data for each of the plurality of gas samples,
   clustering the plurality of gas samples into a plurality of clusters according to a clustering criterion,
   performing a first correction of retention time deviations on the data for the plurality of gas samples between clusters by using the at least one marker molecule as anchor points, so as to reduce retention time deviations between the data for the plurality of gas samples, and
   performing, after said first correction, a second correction of retention time deviations on the data for the plurality of gas samples, so as to further reduce retention time deviations between the data for the plurality of gas samples.

14. A breath analysis system comprising:
a device arranged to receive, for each of a plurality of gas samples obtained as breath exhaled from a subject, chromatographic data indicative of molecule retention times, and
a processor programmed to:
(a) synchronize data for a plurality of gas samples with volatile organic compounds, comprising
receiving, for each of the plurality of gas samples, chromatographic data indicative of molecule retention times,
identifying at least one marker molecule in the chromatographic data for each of the plurality of gas samples,
clustering the plurality of gas samples into a plurality of clusters according to a clustering criterion,
performing a first correction of retention time deviations on the data for the plurality of gas samples between clusters by using the at least one marker molecule as anchor points, so as to reduce retention time deviations between the data for the plurality of gas samples, and
performing, after said first correction, a second correction of retention time deviations on the data for the plurality of gas samples, so as to further reduce retention time deviations between the data for the plurality of gas samples, and
(b) subsequently analyze the chromatographic data for the plurality of gas samples in accordance with an analysis algorithm, and to a provide an output accordingly.

15. The system according to claim 14, further comprising a chromatographic analyzer arranged to receive the plurality of gas samples obtained as breath exhaled from the subject, and to provide chromatographic data indicative of molecule retention times, for each of the plurality of gas samples accordingly.

* * * * *